USO05472344A

United States Patent [19]
Binder et al.

[11] Patent Number: 5,472,344
[45] Date of Patent: Dec. 5, 1995

[54] EXPANSION SCREW FOR TOOTH ADJUSTMENT

[75] Inventors: Friedrich Binder, Kieselbronn; Horst Kalytta; Manfred Rapp, both of Pforzheim; Friedrich-Wilhelm Röhlcke, Kämpfelbach-Bilfingen; Berthold Walter, Remchingen-Singen, all of Germany

[73] Assignee: Dentaurum J.P. Winkelstroeter KG, Ispringen, Germany

[21] Appl. No.: 190,101

[22] PCT Filed: Jul. 27, 1992

[86] PCT No.: PCT/EP92/01698

§ 371 Date: Feb. 2, 1994

§ 102(e) Date: Feb. 2, 1994

[87] PCT Pub. No.: WO93/02629

PCT Pub. Date: Feb. 18, 1993

[30] Foreign Application Priority Data

Aug. 3, 1991 [DE] Germany ............ 41 25 853.3

[51] Int. Cl.⁶ .................................................. A61C 7/00
[52] U.S. Cl. .................................................. 433/7
[58] Field of Search ............................... 433/6, 7

[56] References Cited

U.S. PATENT DOCUMENTS

| | | | |
|---|---|---|---|
| 4,347,054 | 8/1982 | Kraus et al. | 433/7 |
| 4,482,318 | 11/1984 | Forster | 433/7 |
| 4,571,177 | 2/1986 | Dahan | 433/7 |
| 4,917,601 | 4/1990 | Williams | 433/7 |

FOREIGN PATENT DOCUMENTS

| | | | |
|---|---|---|---|
| 0304756 | 8/1988 | European Pat. Off. | A61C 7/00 |
| 824832 | 7/1949 | Germany . | |
| 1932323 | 6/1965 | Germany . | |
| 2712696 | 9/1978 | Germany . | |
| 2722611 | 11/1978 | Germany | 433/7 |
| 526301 | 9/1972 | Switzerland | A61C 7/00 |
| 641139 | 8/1950 | United Kingdom | 433/7 |
| 718385 | 11/1954 | United Kingdom | 433/7 |

Primary Examiner—Nicholas D. Lucchesi
Attorney, Agent, or Firm—Leydig, Voit & Mayer, Ltd.

[57] ABSTRACT

Expansion screw for tooth adjustment having two expansion screw body members each embeddable in a plastic palate plate, these body members being provided with retention grooves for anchoring in the plastic of these palate plates, also having a threaded spindle and two guide pins, wherein the threaded spindle has spindle sections with opposite threads on either side of a central section, these spindle sections engaging in corresponding threaded bores of the expansion screw body members, and wherein the latter have guide openings for the passage of the guide pins extending parallel to the threaded spindle. In order to reduce the size of the two expansion screw body members, the latter are of a hat-shaped design in the side view and provided at their central regions with retention grooves and, in addition, at their facing inner end faces with recesses for accommodating the central section of the threaded spindle, these recesses being designed such that these end faces can abut on one another when the threaded spindle is turned and that in this state of the expansion screw the central section of the threaded spindle provided with a tool attachment point is accessible from the outside.

17 Claims, 4 Drawing Sheets

EXPANSION SCREW FOR TOOTH ADJUSTMENT

FIELD OF THE INVENTION

The invention relates to an expansion screw for tooth adjustment having two expansion screw body members each embeddable in a plastic palate plate, these body members being provided with retention means for anchoring in the plastic of these palate plates, also having a threaded spindle and at least one guide pin, wherein the threaded spindle has spindle sections with opposite threads on either side of a central section provided with a point of attachment for a tool for turning the threaded spindle, these spindle sections engaging in channels provided with corresponding internal threads in the expansion screw body members for altering the distance of the two expansion screw body members from one another, and wherein the expansion screw body members have guide openings for the passage of the guide pin extending parallel to the threaded spindle.

BACKGROUND OF THE INVENTION

There are two current types of expansion screws with which the forces exerted by the expansion screw are to be transferred in various ways onto the tooth or teeth, the position of which is intended to be corrected: In expansion screws of a first type, the relevant expansion screw is embedded in a palate plate cast from casting resin and divides the palate plate into two parts such that one of the two expansion screw body members of the expansion screw is located in each palate plate part and so the distance of the two palate plate parts from one another can be altered by turning the threaded spindle of the expansion screw. During the casting of the palate plate, for example, clasp-like anchoring elements are secured therein and these elements engage on teeth so that the forces of the expansion screw are transferred to the relevant teeth via the palate plate parts. Such an expansion screw of this type is, for example, illustrated in FIG. 3 of DE-PS 33 01 753. With the second type of expansion screw, two rods or stiff wires are secured, in particular welded, to each of the two expansion screw body members and the relevant expansion screw body member can be anchored by these rods or wires directly onto metal bands secured to the teeth. An expansion screw of this type is illustrated, for example, in FIG. 2 of U.S. Pat. No. 4,917,601.

When in the above or in the following mention is made of a tooth adjustment or of the correction of the position of a tooth or several teeth, this is to be understood as also including, for example, the separation of the mid-palatal suture since a mid-palatal suture separation also results, of course, in an alteration of the tooth position.

SUMMARY OF THE INVENTION

As expressed at the outset, the present invention deals with expansion screws of the first type, i.e. with expansion screws which are used in conjunction with a plastic palate plate, during the production of which the two expansion screw body members are embedded in the casting resin of the palate plate.

An expansion screw of the type specified at the outset is known; this known expansion screw corresponds to that according to DE-PS 33 01 753 but is provided with retention means in the form of short, straight grooves which—in the side view of the expansion screw—are arranged in front of and behind the threaded spindle as well as at the outer narrow sides of the two expansion screw body members.

This known expansion screw has two guide pins arranged on either side of the threaded spindle and these pins are guided for displacement in guide openings of both expansion screw body members. The latter have a rectangular cross section along the plane defined by the longitudinal central axes of the threaded spindle and guide pins, and the central section of the threaded spindle has the shape of a thickened, circular-cylindrical collar (spindle head) with a transverse bore for the insertion of a pivot pin, with which the threaded spindle can be turned. The guide openings of the two expansion screw body members each have the shape of a recessed bore, the first section of which facing the spindle head has a diameter corresponding to the diameter of the guide pins and is followed by a bore section of larger diameter, into which head-shaped, thickened ends of the guide pins, which act as stops, can be inserted when the expansion screw body members are moved apart due to turning of the threaded spindle until these stops abut on the shoulders which form the second bore sections at the transition to the first bore sections. In the case of this known expansion screw, the maximum path of an expansion screw body member is equal to half the length of a guide pin (calculated without its thickened end) less the length of the first bore section of smaller diameter and less half the width of the spindle head (measured in the longitudinal direction of the threaded spindle), provided that both guide pins are of equal length and at the most as long as the threaded spindle.

Since expansion screws of this type are worn in the mouth where every millimeter is of importance in view of the cramped spatial conditions, depending on the position of the tooth or teeth which is or are to be corrected, the object underlying the invention was to provide an expansion screw of the type mentioned at the outset which is smaller than the known expansion screw described above, at a predetermined maximum path of expansion, without the smaller size impairing the function of the expansion screw (in this respect, the maximum path of expansion is to be understood as the maximum possible alteration in the distance between the facing inner end faces of the expansion screw body members).

This object may be accomplished in accordance with the invention in that the expansion screw body members are stepped at their outer end faces remote from one another such that a first region of each expansion screw body member accommodating the channel protrudes in the longitudinal direction of the threaded spindle beyond a second region of the relevant expansion screw body member accommodating the guide opening for the guide pin, that the retention means are provided at the first regions of the two expansion screw body members, that the channels are designed at the facing inner end faces of the two expansion screw body members to accommodate the central section of the threaded spindle and so in an initial state of the expansion screw these inner end faces are adapted to abut at least almost against one another, and that the expansion screw body members have at least one recess, the tool attachment point of the threaded spindle being accessible from the outside through this recess in the initial state of the expansion screw.

While the expansion screw body members of both the expansion screw according to DE-PS 33 01 753 discussed above and the expansion screw according to U.S. Pat. No. 4,917,601 are block-shaped in design, i.e. rectangular in the side view, the inventive expansion screw is much more delicate due to its stepped expansion screw body members. In addition, a relatively large gap is avoided between the expansion screw body members due to the inventive design of the expansion screw—if special measures are not taken, the casting resin flows into this gap in the known expansion screws during production of the palate plate and this can have a disadvantageous effect on the actuation of the threaded spindle. Finally, it is also possible to save on material for the expansion screw body members during the production of the inventive expansion screw and this is of importance, in particular, when the body members are produced from an expensive material. Any saving on material also results, of course, in a reduction in the weight of the expansion screw. On the other hand, the reduction in size of the expansion screw body does not have any disadvantageous effects on the quality of the sliding guidance of the guide pin in the guide openings of the expansion screw body members owing to the inventive arrangement of the retention means at the first regions of the two expansion screw body members comprising the threaded spindle. Considerable forces are to be transferred from the expansion screw body members to the parts of the palate plate. If retention means were provided at the relatively thin second regions of the expansion screw body members, in particular at the outer narrow sides of these second regions of the expansion screw body members, there would be the risk, due to the forces to be transferred, of the narrow second regions of the expansion screw body members being deflected or even bent in relation to the first regions comprising the threaded spindle and, therefore, the guide openings being canted on the guide pin as a result of these forces.

Certain features of the inventive solution are, indeed, known from the state of the art but the known expansion screws could still not anticipate the inventive combination because none of the known expansion screws teaches how an expansion screw which is to be embedded in a palate plate is to be designed in order for it to be of as delicate a construction as possible, on the one hand, but, on the other hand, to ensure a good sliding guidance for the guide pin despite the considerable forces to be transferred from the expansion screw to the palate plate parts. With respect to the state of the art, reference is also made in detail to the following known expansion screws:

The expansion screw according to U.S. Pat. No. 4,917,601 is, as already mentioned, an expansion screw having rods welded to its expansion screw body members, with which the expansion screw is intended to be anchored directly to metal bands attached to the teeth. The two expansion screw body members of this known expansion screw have at their facing ends recesses for accommodating the spindle head of the threaded spindle so that in the initial state of the expansion screw the inner end faces of the two expansion screw body members abut on one another and the recesses form a window, through which, in the initial state of the expansion screw, the tool attachment point of the spindle head is accessible from the outside. As already mentioned, the two expansion screw body members of this known expansion screw are, however, of a block-type design, i.e. approximately rectangular in the side view, and retention means are not provided on the expansion screw body members because the latter are anchored by the specified rods directly on teeth.

The same is true of another known expansion screw, which results from DE-PS 27 12 696 and essentially differs from the expansion screw according to U.S. Pat. No. 4,917,601 only in that two of the four rods serving to directly anchor the expansion screw to teeth form guide pins at the same time.

DE-GM 1 932 323 discloses an expansion screw provided for embedding in a plastic palate plate, the expansion screw body members of which accommodate a small plate-like expansion screw holder between them when the expansion screw is embedded in a palate plate. This holder encloses the spindle head of the threaded spindle such that the expansion screw body members can be brought closer to one another only to such an extent that the distance between them is equal to the thickness of the expansion screw holder or equal to the axial length of the spindle head. The two expansion screw body members of this known expansion screw are of an approximately "hat-shaped" design in the side view and each have a central first region which comprises the threaded spindle as well as two flat second regions which extend away from this central region towards the side and have guide openings for guide pins. Retention means are not provided at all in this known expansion screw.

Finally, DE-PS 824 832 discloses an expansion screw of a completely different type having two expansion screw body members which are block-shaped in design, i.e. approximately rectangular in the side view, and which each have at their facing inner ends a recess for accommodating the spindle head of the threaded spindle. These recesses are each followed by a stepped bore, the inner part of which, which is smaller in diameter, is penetrated by the threaded spindle and the outer part of which, which is larger in diameter, bears a nut for the threaded spindle which is pressed by a compression spring against the shoulder formed by the bore. In order to hold the two pressure springs in the expansion screw body members, a cover is placed on each of their outer end faces which face away from one another. One of these covers is penetrated by two guide pins which are secured in position in the expansion screw body member belonging to the other cover. Annular grooves extend around the two block-shaped expansion screw body members and these grooves form retention means for anchoring the expansion screw body members in the parts of a palate plate. An expansion screw holder is not provided in this known expansion screw.

The inventive solution also allows the maximum path of expansion of the inventive expansion screw to be increased, by corresponding dimensioning of the thickness (measured in the longitudinal direction of the threaded spindle) of the second regions of the expansion screw body members accommodating the guide openings for the guide pin or the guide pins, such that it exceeds that of the known expansion screw according to DE-PS 33 01 753 (when the length of threaded spindle and guide pin or guide pins is the same), namely by the width of the central section of the threaded spindle (of the spindle head of the known expansion screw) measured in the longitudinal direction of the threaded spindle, because in the initial state of the inventive expansion screw its expansion screw body members can completely accommodate the central section of the threaded spindle—it is then only necessary to design the expansion screw body members such that the tool attachment point of the threaded spindle is still adequately accessible for a corresponding tool when the two expansion screw body members have been brought so close to one another that they abut on one another.

When it has been stated in the above that the facing inner end faces of the two expansion screw body members are intended to be able to abut on one another, this certainly does not mean that these inner end faces each form a plane or even a plane extending at right angles to the spindle axis, and in this respect reference can be made to the embodiments of the inventive expansion screw which will be described at a later stage.

In the case of the inventive expansion screw, the guide pin is or the guide pins are intended to be freely displaceable in both expansion screw body members, when any end stops which may be provided are left out of account.

The invention does not presuppose that the central section of the threaded spindle which is provided with the tool attachment point is designed as a thickened spindle head; this central section of the threaded spindle could have the same or even a slightly smaller outer diameter than the threaded sections provided with threads since it is only important that the recess in at least one of the two expansion screw body members forms a type of window, through which a tool can be applied to the threaded spindle for turning this spindle, on at least one side, preferably on both sides of the expansion screw body members which have been brought together.

A minimum length of the guide pin or the guide pins (at a predetermined maximum path of expansion of the expansion screw) results when in the initial state of the expansion screw the inner end faces of the expansion screw body members abut on one another in the region of their guide openings.

The sections of the threaded spindle provided with opposite threads could be immediately adjacent one another without a thread-free region of the threaded spindle when a transverse bore is selected as tool attachment point. In this case, the internal threads of the expansion screw body members could extend as far as their facing, inner end faces. In inventive expansion screws, in which the central section of the threaded spindle is designed as a thickened spindle head, the channel of at least one of the expansion screw body members has, however, adjacent its inner end face a recess for accommodating the central section of the threaded spindle which is enlarged in relation to its internal thread. In this connection, reference is made to the following: In principle, the only important feature for the functioning of an expansion screw is the change in the distance of the two expansion screw body members from one another; for this reason, it would, for example, also be possible, in the initial state of an expansion screw, to accommodate the spindle head of its threaded spindle completely in one of the two expansion screw body members, as is shown, for example, in DE-PS 27 12 696. It is then sufficient to provide only one of the two expansion screw body members with a recess for accommodating the central section of the threaded spindle which is enlarged in relation to its internal thread and also to provide a recess, through which the tool attachment point of the threaded spindle is accessible from the outside in the initial state of the expansion screw, only in this expansion screw body member. For the reasons explained above, the two opposite threads of the threaded spindle need not have the same thread pitch (the same applies to the internal threads of the expansion screw body members). This shows that the central section of the threaded spindle need not be located exactly in the center of the threaded spindle and in the initial state of the expansion screw can be inserted into only one of the two expansion screw body members. In a preferred embodiment of the inventive expansion screw, the channels of both expansion screw body members do, however, have an enlarged recess for respectively accommodating half the central section of the threaded spindle designed as a spindle head.

The above explanations show that an essential constructional feature of the inventive expansion screw can also be defined such that the channels for the threaded spindle, which are provided in the expansion screw body members, are designed such that in the initial state of the expansion screw they accommodate the central section of the threaded spindle except for a window, through which the tool attachment point of the threaded spindle is accessible from the outside, and that the guide surfaces of the guide openings for the guide pin or the guide pins extend as far as those regions of the inner end faces of the expansion screw body members which abut at least almost against one another in the initial state of the expansion screw.

With the inventive expansion screw embodiments are also preferred, in which two guide pins arranged on either side of the threaded spindle are provided; in this case, it is recommended that the expansion screw be designed such that each expansion screw body member has an approximately hat-shaped cross section along the plane defined by the longitudinal central axes of threaded spindle and at least one of the guide pins. The second regions of the respective expansion screw body member accommodating the guide openings then form, so-to-speak, the brim of the hat.

It is particularly advantageous for the expansion screw to be designed to be symmetrical to a longitudinal central plane which extends through the longitudinal central axis of the threaded spindle and at right angles to that plane which is defined by the longitudinal central axes of threaded spindle and guide pins. According to a further feature of the invention, the expansion screw is designed to be symmetrical to the plane last mentioned.

To prevent the guide pins from falling out of the expansion screw body members, an embodiment is recommended, in which the guide pin is designed as a cylindrical body, the two ends of which deviate in design from the cylindrical shape to form stops interacting with the outer end faces of the expansion screw body members. In this respect, it is recommended that these stops be formed by cutting notches into the end faces of the guide pins.

In order to hold an expansion screw in the correct position during the casting of the palate plate it is customary for the expansion screw to be provided with a so-called expansion screw holder which is a small plastic plate which has openings for the passage of the threaded spindle and the guide pins and comprises the spindle head in the known expansion screws and is arranged between the expansion screw body members brought together to the smallest possible distance between them. In this connection, reference is, however, made to the fact that an expansion screw holder is not absolutely necessary because the expansion screw could also be fixed with adhesive wax to the mold for the casting of the palate plate and the spindle head could be covered with wax to prevent its tool attachment point being covered over by the casting resin.

The invention now suggests a completely different course to follow if an inventive expansion screw is intended to be provided with an expansion screw holder: An expansion screw holder is suggested which encloses the expansion screw body members drawn together and which lies completely outside the interface or interstice between the expansion screw body members and preferably covers the tool attachment point of the threaded spindle. This means that the expansion screw holder does not obstruct any complete drawing together of the two expansion screw body members. For particularly advantageous embodiments, it is suggested that the expansion screw holder be designed such that it completely encloses the two expansion screw body members, which are drawn together, in the region of the interstice located between them and thereby covers the window or windows which is or are formed by the recesses provided on the inner end faces of the expansion screw body members.

The expansion screw holder then prevents the casting resin from penetrating the interstice between the two expansion screw body members as well as any covering over of the tool attachment point of the threaded spindle by the casting resin.

If, in the case of an expansion screw having such an expansion screw holder, retention means were to be provided on the outer narrow sides of the relatively thin, second regions of the expansion screw body members, these retention means would be covered by the expansion screw holder at least to a large extent which would preclude a good anchoring of the expansion screw body members in the palate plate parts. Owing to the inventive arrangement of the retention means at the first regions of the expansion screw body members enclosing the threaded spindle, the expansion screw body members may be well anchored in a palate plate even though the expansion screw holder encloses the expansion screw body members drawn together and is not, as is the case in the known expansion screws, located between the expansion screw body members.

In order to simplify the assembly of the expansion screw together with the expansion screw holder and to ensure that the expansion screw holder reliably covers the tool attachment point of the threaded spindle, it is, finally, recommended that at least one of the two expansion screw body members be provided with a stop for the expansion screw holder which acts in the direction of the threaded spindle axis.

A particularly efficient production of the inventive expansion screw is made possible by an embodiment, in which the two expansion screw body members are of identical design, apart from their internal threads and a stop possibly provided for the expansion screw holder.

The retention means could have the shape of knurled zones or, for example, etched, rough surface regions. With a view to a particularly good anchoring of the expansion screw body members in the palate plate parts, groove-like retention means are, however, preferred. In this respect, it has proven to be particularly advantageous and effective for the retention grooves to be designed as annular grooves which extend around the first regions of the two expansion screw body members which comprise the threaded spindle.

Additional advantages, features and details of the invention result from the following description as well as the attached drawings of three particularly preferred embodiments of the inventive expansion screw; in the drawings:

DETAILED DESCRIPTION OF A PREFERRED EMBODIMENT

Figure 1:
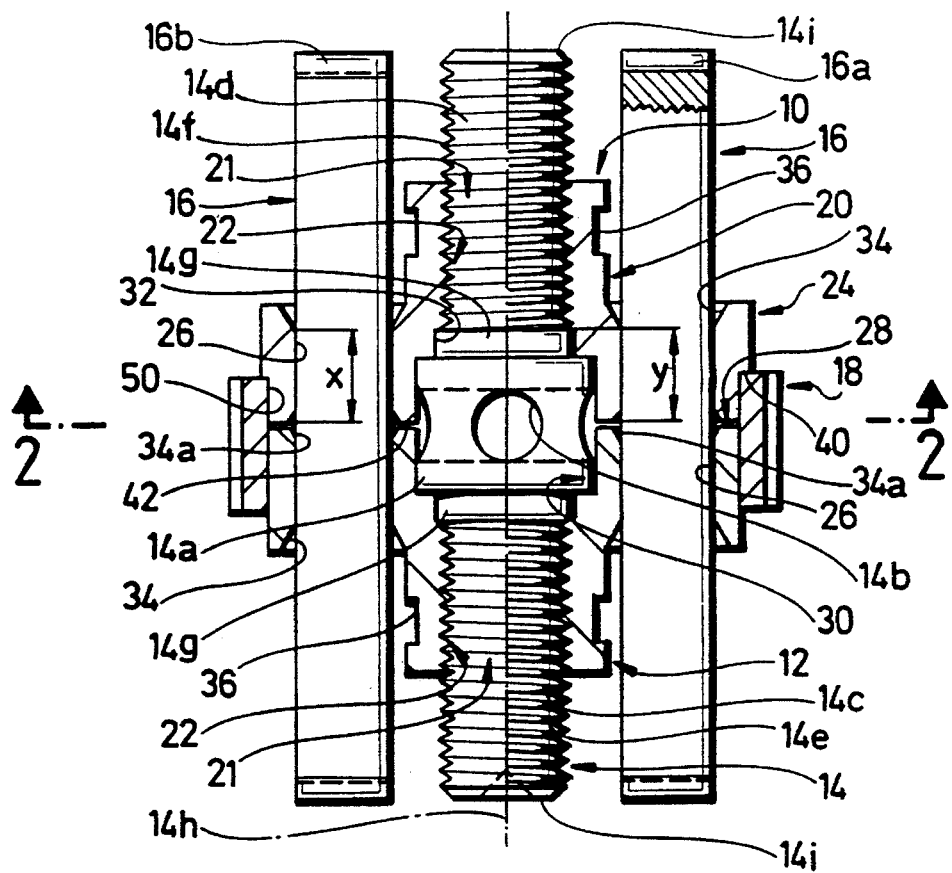
FIG. 1 shows a longitudinal section through the first expansion screw with attached expansion screw holder, namely a section along line 1—1 in FIG. 2.

The expansion screw according to FIGS. 1 to 5 consists of a first and a second expansion screw body member 10 and 12, respectively, a threaded spindle 14, two guide pins 16 and an expansion screw holder 18.

The threaded spindle 14 has a thickened spindle head 14a which is centrally arranged according to the invention and has two centrally arranged transverse bores 14b extending at right angles to one another as well as two threaded sections 14c and 14d arranged on either side of the spindle head and having opposite threads 14e and 14f of the same pitch. The latter end at transition regions 14g which are designed to be circular-cylindrical and border on the spindle head 14a, which is designed to be rotationally symmetrical to the spindle axis 14h, and preferably have the same external diameter as the threaded sections 14c and 14d. Instead of the illustrated transition region 14g, a groove (not shown) could also be used in which the adjacent thread 14e or 14f ends.

In the illustrated, preferred embodiment, the guide pins 16 are circular-cylindrical in design—apart from their end regions—although they could also have a different cross section, i.e. they could, for example, be designed in the shape of a prism. Following the assembly of the expansion screw, notches 16a are cut into the end faces of the guide pins 16 and these result in a slight increase in the circumferential dimensions of the ends of the guide pins so that these ends form stops which have been designated 16b in FIG. 1—the deviations in the outer contour of these stops in comparison with the outer contour of the actual guide pins 16 are so slight that they are not apparent in FIG. 1.

Figure 3:
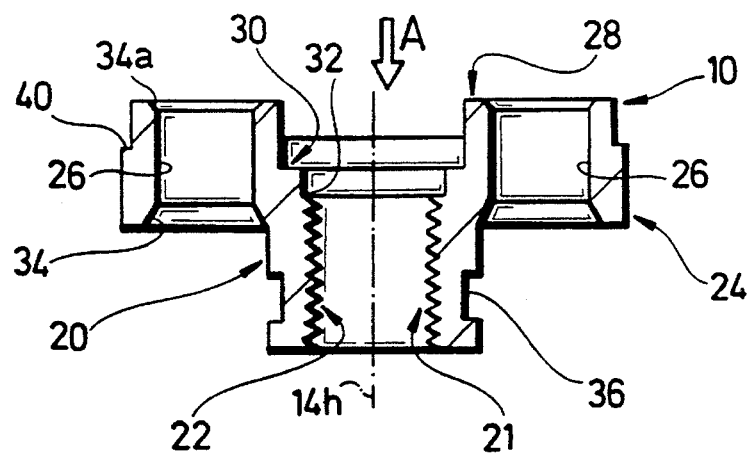
FIG. 3 shows the expansion screw body member illustrated at the top of FIG. 1 in the same section as in FIG. 1.
Figure 4:
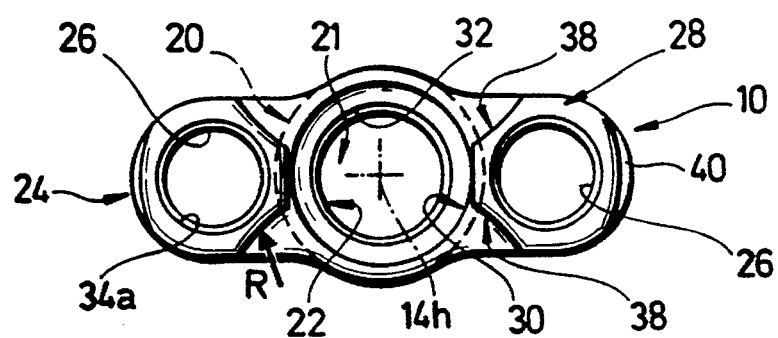
FIG. 4 shows this expansion screw body member seen in the direction of arrow "A" in FIG. 3.
Figure 5:
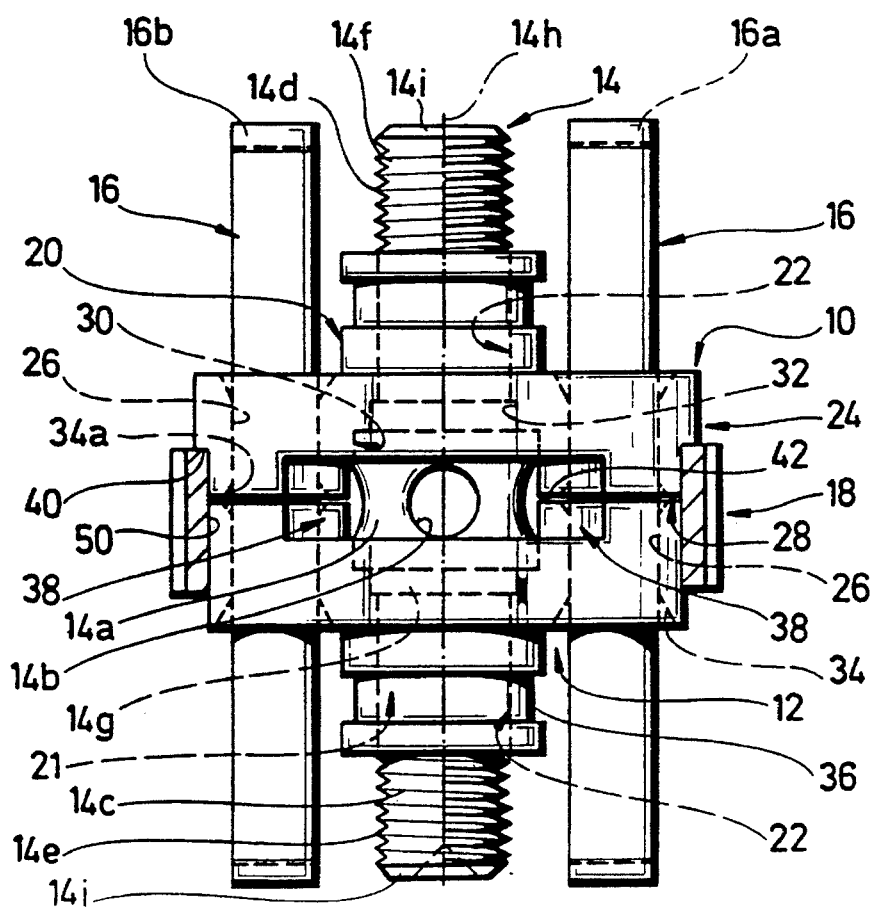
FIG. 5 is a plan view onto this expansion screw.

The first expansion screw body member 10, illustrated at the top in FIG. 1, will now be explained in greater detail on the basis of FIGS. 3–5.

This expansion screw body member has on each side of a first region 20, which is of a neck-shaped design in accordance with the invention and in which a channel 21 provided with an internal thread 22 is located, a second region 24 having a guide opening 26 for one of the guide pins 16. A recess 30 extends into the expansion screw body member from an inner end face 28 of the expansion screw body member located in the interior of the expansion screw. The shape of this recess is, in accordance with the invention, adapted to that of the spindle head 14a such that the recess 30 can accommodate approximately half the spindle head 14a and the latter can turn in this recess. A recess 32 is provided between the internal thread 22 and the recess 30 and this is adapted to the dimensions of the transition region 14g of the threaded spindle 14 so that this transition region can turn in the recess 32. At the outer end face of the expansion screw body member 10 lying opposite the inner end face 28 the guide openings 26 are provided with countersinks 34 into which the stops 16b of the guide pins 16 can enter. Finally, a circular ring-shaped retention groove 36 is provided in the outer circumference of the neck-shaped first region 20.

In accordance with the invention, the expansion screw body member 10 is provided on each of its two broad sides (upper and lower sides according to FIG. 4) with a recess 38 which has been produced, in particular, as a recess manufactured with a radius R. When the expansion screw body members 10 and 12 are drawn together, i.e. abut on one another (as illustrated in FIG. 1), these recesses 38 of the two expansion screw body members form on each expansion screw side a type of window, through which the spindle head 14a is exposed, so that a pin or another suitable tool can be inserted through this window into one of the transverse bores 14b and, with the aid of this pin, the threaded spindle 14 can be turned through an angle of rotation of, for example, 90°.

The recesses 38 can extend into the expansion screw body member 10 in the direction of the spindle axis 14h, proceeding from the inner end face 28, to such an extent that the spindle head 14a is exposed in its entire width (measured in the direction of the spindle axis) through the windows formed by the recesses 38. However, embodiments are preferred, in which the recesses 38 extend into the expansion screw body member 10 in axial direction only to such an extent that the windows formed by these recesses 38 only expose that region of the spindle head 14a in which the transverse bores 14b are located, i.e. the axial extension of these windows is equal to the diameter of the transverse bores 14b or only slightly greater.

The second expansion screw body member 12 is identical to the first expansion screw body member 10 as so far described in the above, except for opposite internal threads 22. The difference between the two expansion screw body members 10 and 12 consists only in at least one stop or preferably two stops 40 formed on the first expansion screw body member 10 for the expansion screw holder 18 in order to ensure that the latter covers the interstice 42 between the two expansion screw body members 10 and 12 as well as the two windows formed by the recesses 38. When the expansion screw is embedded in a palate plate produced from a casting resin, the expansion screw is in the state shown in FIG. 1, i.e. the two expansion screw body members 10 and 12 are drawn together and abut on one another and so it can be ensured due to the covering formed by the expansion screw holder 18 that no casting resin can flow into the interstice 42 and into the transverse bores 14b.

Figure 2:
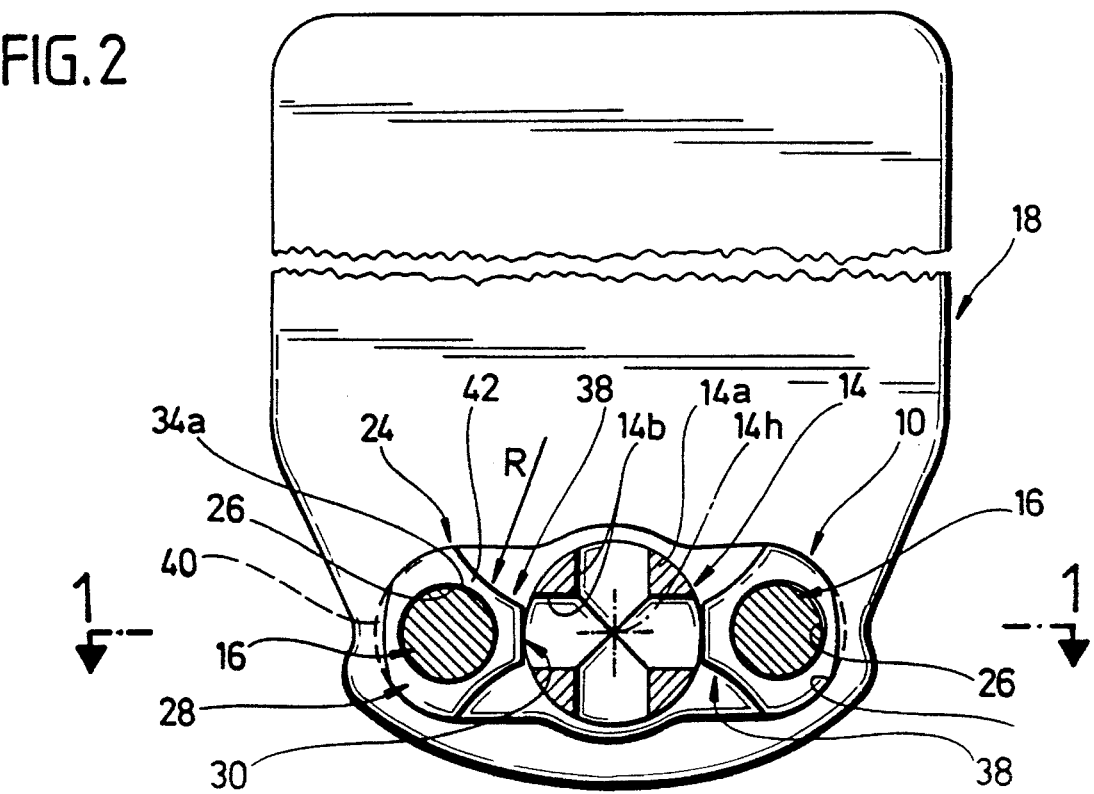
FIG. 2 shows a section through this expansion screw with expansion screw holder along line 2—2 in FIG. 1.

The expansion screw holder 18 shown in FIGS. 1 and 2 has, as already mentioned, the shape of a small plastic plate with an opening 50, the shape of which corresponds to the outer contour of the expansion screw body formed by the two expansion screw body members 10 and 12, namely the outer contour when viewing the expansion screw body in the direction of the spindle axis 14h.

The expansion screw holder 18 is, of course, removed before the expansion screw is actuated. By turning the threaded spindle 14 the two expansion screw body members 10 and 12 can then be moved apart to such an extent until the stops 16b of the guide pins 16 enter the countersinks 34 of the two expansion screw body members 10, 12 and come to rest on these expansion screw body members. For this purpose, the threaded spindle 14 must, of course, be of such a length that its threaded sections 14c and 14d still engage in the internal threads 22 of the two expansion screw body members 10, 12.

Figure 6:
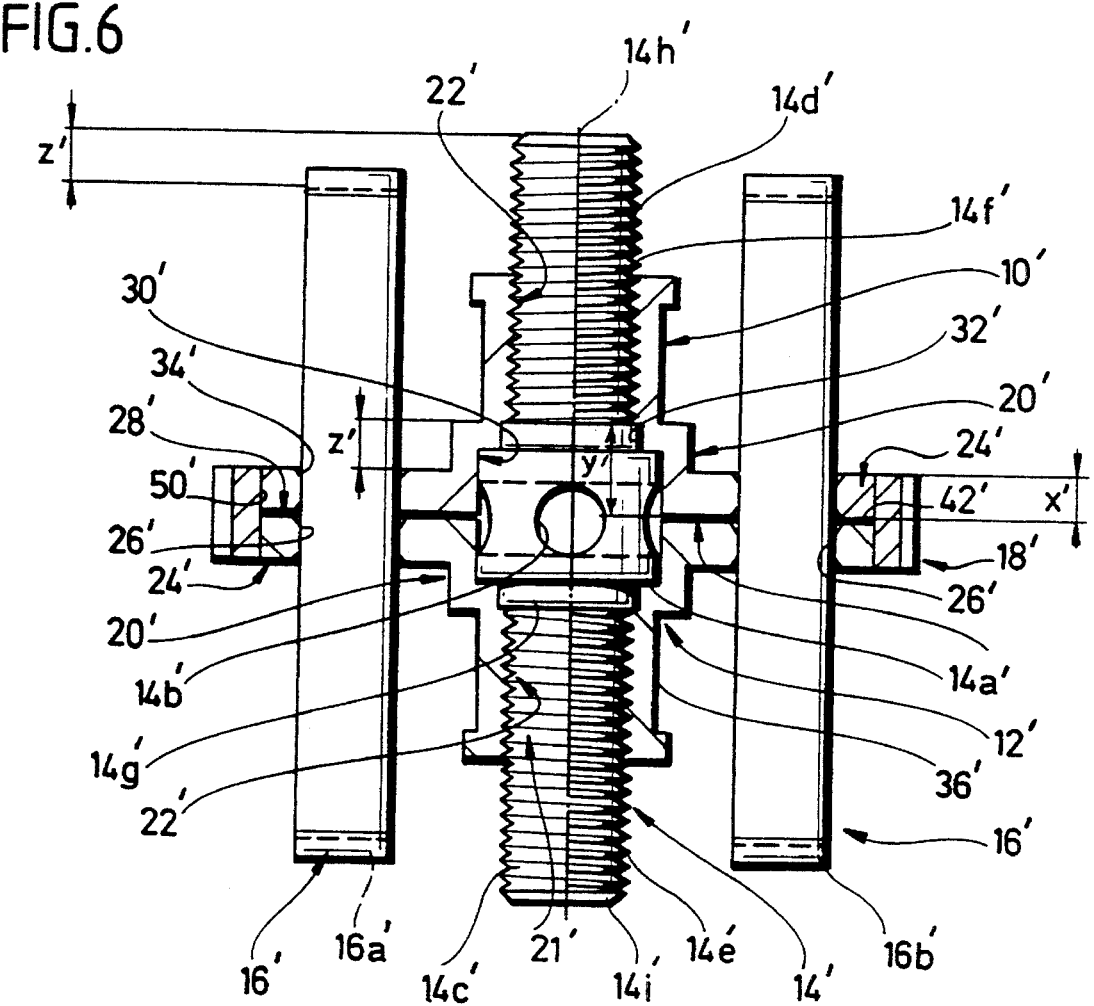
FIG. 6 is an illustration of the second embodiment of the inventive expansion screw corresponding to FIG. 1.

FIG. 6 shows the second embodiment in a section corresponding to FIG. 1, and the various parts of this expansion screw have been designated with the same reference numerals as in FIG. 1 but with the addition of a prime. Whereas, however, the threaded spindle 14 and the guide pins 16 in the embodiment according to FIG. 1 are of the same length because, in accordance with the invention, the guide length "x" of the guide openings 26 corresponds in this embodiment to half the overall length of the spindle head 14a and the two transition regions 14g (measured in the direction of the spindle axis 14h), i.e. in other words the length of that part of the corresponding expansion screw body member which is not provided with the internal thread 22, the threaded spindle 14' of the embodiment according to FIG. 6 is, according to the invention, longer than the guide pins 16', namely for the following reason: In the embodiment according to FIG. 6, the guide length "x'" of the guide openings 26' of the expansion screw body members 10', 12' is, according to the invention, smaller than the measurement "y'", namely by the measurement "z'", and the thread 14e' or 14f', respectively, of the threaded spindle 14' is longer than the corresponding thread of the threaded spindle 14 by this measurement "z'". This means that the threaded spindle 14' is longer than the guide pins 16' by the double amount of this measurement "z'".

When mention is made in the above of the length of the threaded spindle and the length of the guide pins, the lengths of the stops 16a and 16a', respectively, of the guide pins and the lengths of the thread-less end regions 14i and 14i', respectively, of the threaded spindle have been left out of consideration just as much as any narrow gap which may be present between the two expansion screw body members instead of the interstice 42 or 42' and which can result, in unfavourable cases, due to angular offset displacements of the threads 14e, 14f or 14e', 14f' and/or of the internal threads 22 or 22'.

Under this precondition, a comparison of the two embodiments according to FIGS. 1 and 6 results in the fact that, according to the invention, the length L of the threaded spindle is $$L=l+(2y-2x),$$

wherein l is the length of the guide pins, x the guide length of a guide opening 26 (disregarding the depth of a countersink 34a at the inner end face 28) and y half the overall length of the thread-less central section of the threaded spindle, whereby in the embodiments illustrated this thread-less central section is composed of the spindle head 14a or 14a' and the thread-less transition regions 14g or 14g'.

Figure 7:
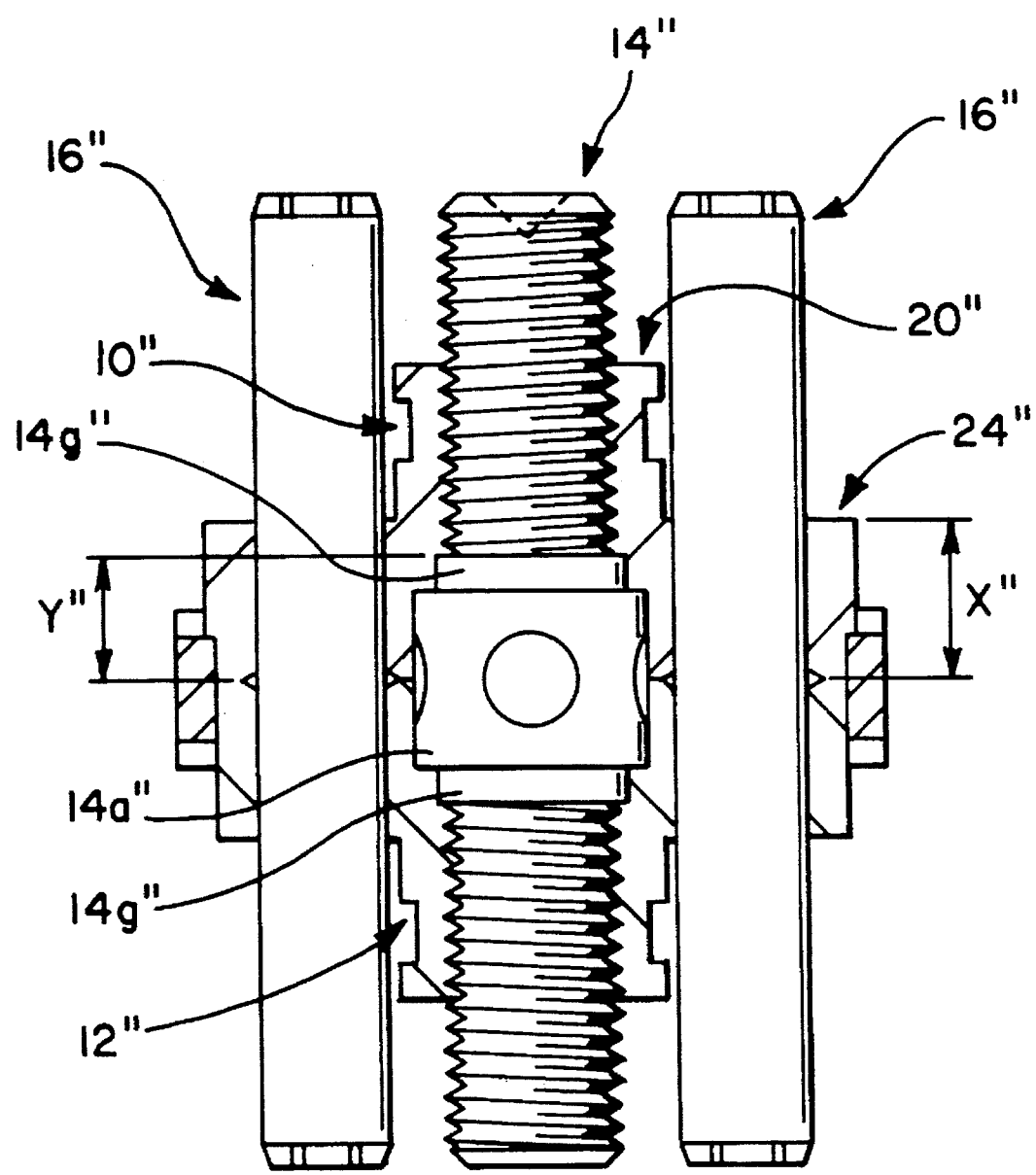
FIG. 7 is an illustration of the third embodiment corresponding to FIG. 1.

Whereas the embodiments according to FIGS. 1 to 6 result in particularly large paths of expansion (at predetermined lengths of threaded spindles and guide pins), the expansion screw body members of the embodiment according to FIG. 7 have an increased stability. In FIG. 7, all the parts have been given the same reference numerals as in FIGS. 1 to 5 but with the addition of a double prime so that, in the following, only the differences between the embodiment according to FIG. 7 and the embodiment according to FIGS. 1 to 5 will be explained.

In the embodiment according to FIG. 7, namely, half the axial length of the spindle head 14a" plus the axial length of a thread-less transition region 14g", i.e. the length y", is smaller than the guide length x" (also when taking a countersink 34" into consideration) in order to increase the rigidity at the transition from the second regions 24" to the first region 20" of the expansion screw body members. Moreover, an increase in the thickness of the second regions of the expansion screw body members results in the advantage that the latter can be reliably gripped at their side edges by automatic gripping means during automatic assembly of the expansion screw.

In this embodiment, the axial length of the thread-less central section of the threaded spindle is, therefore, somewhat larger than the sum of the thicknesses of the second regions 24" of the two expansion screw body members.

We claim:

1. An expansion screw for tooth adjustment having two expansion screw body members each embeddable in a plastic palate plate, the body members being provided with retention means for anchoring in the plastic of said palate plate, also having a threaded spindle and at least one guide pin, wherein the threaded spindle has spindle sections with opposite threads on either side of a central section provided with a point of attachment for a tool for turning the threaded spindle, the spindle sections engaging in channels provided with corresponding internal threads in the expansion screw body members for altering the distance of the two expansion screw body members from one another, and wherein the expansion screw body members have guide openings for the passage of said at least one guide pin extending parallel to the threaded spindle, each expansion screw body member being stepped at an outer end face remote from an outer end face of the other body member such that a first region of said expansion screw body member accommodating one of the channels protrudes in the longitudinal direction of the threaded spindle beyond a second region of said expansion screw body member accommodating the guide opening for said at least one guide pin wherein the retention means are arranged at the first regions of the two expansion screw body members, and the channels are designed at facing inner end faces of the two expansion screw body members to accommodate the central section of the threaded spindle whereby in a non-expanded initial state of the expansion screw said inner end faces are adapted to abut at least almost against one another, and wherein the expansion screw body members have at least one recess through which, in the initial state of the expansion screw, the tool attachment point of the threaded spindle is accessible from the outside of the expansion screw.

2. The expansion screw as defined in claim 1, wherein during the initial state of the expansion screw the inner end faces of the expansion screw body members abut at least almost on one another in the region of the guide openings.

3. The expansion screw as defined in claim 1, wherein the channel of at least one of the expansion screw body members has adjacent its inner end face a recess enlarged in relation to its internal thread for accommodating the central section of the threaded spindle.

4. The expansion screw as defined in claim 3, wherein the channels of the two expansion screw body members each comprise an enlarged recess for respectively accommodating half the central section of the threaded spindle.

5. The expansion screw as defined in claim 1, wherein the second region of each of said body members has a wall thickness measured in the longitudinal direction of the spindle and wherein the first region of each of said body members protrudes beyond the second region by at least said wall thickness.

6. The expansion screw as defined in claim 1, wherein two guide pins arranged on either side of the threaded spindle are provided and each expansion screw body member has an approximately hat-shaped cross section along the plane defined by the longitudinal central axes of the threaded spindle and at least one of the guide pins.

7. The expansion screw as defined in claim 1, wherein said at least one guide pin is designed as a cylindrical body, having two ends deviating in shape from that of the cylindrical body to form stops interacting with the outer end faces of the expansion screw body members.

8. The expansion screw as defined in claim 1, wherein in said initial state of the expansion screw, an interstice is provided between said inner end faces of the body members, said expansion screw further comprising an expansion screw holder enclosing at least partially the expansion screw body members drawn together, said holder lying completely outside the interstice between the expansion screw body members.

9. The expansion screw as defined in claim 8, wherein the expansion screw holder covers the tool attachment point of the threaded spindle.

10. The expansion screw as defined in claim 8 wherein the expansion screw holder covers the interstice between the expansion screen body members.

11. The expansion screw as defined in claim 8 wherein the expansion screen holder covers the interstice between the expansion screen body members at least in the initial state of the expansion screw.

12. The expansion screw as defined in claim 1, wherein the two expansion screw body members are of substantially identical outer shape.

13. The expansion screw as defined in claim 1, wherein at least one retention means comprises an annular groove provided at the circumference of the first region of each expansion screw body member.

14. The expansion screw as defined in claim 1, wherein the threaded spindle and said at least one guide pin are of equal length.

15. The expansion screw as defined in claim 1, wherein the threaded spindle is longer than said at least one guide pin.

16. The expansion screw as defined in claim 1, wherein said guide openings define guide faces for said at least one guide pin and said guide faces end at guide opening neighboring regions of said inner end faces, said regions adapted to abut one another in the initial state of the expansion screw.

17. The expansion screw as defined in claim 1, further comprising a spindle head formed by said central section of the threaded spindle, the thickness of said spindle head measured in the longitudinal direction of the threaded spindle being at least equal to the sum of the thicknesses of the second regions of the two expansion screw body members adjacent one another.

* * * * *